United States Patent [19]

Tezón et al.

[11] Patent Number: 5,736,346
[45] Date of Patent: Apr. 7, 1998

[54] INDUCTION OF THE ACROSOME REACTION TO EVALUATE THE FERTILIZATION CAPABILITY OF MAMMALIAN SPERM USING A DENDRIMER SUGAR CONJUGATE

[75] Inventors: Jorge Guillermo Tezón, Buenos Aires, Argentina; Adriano Brandelli, Porto Alegre, Brazil

[73] Assignee: Fundacion Instituto de Biologia y Medicina Experimental, Argentina

[21] Appl. No.: 742,867

[22] Filed: Nov. 1, 1996

Related U.S. Application Data

[63] Continuation of Ser. No. 213,195, Mar. 14, 1994, abandoned.

[51] Int. Cl.$^6$ .................................................... G01N 33/567
[52] U.S. Cl. ............................ 435/7.21; 435/2; 424/1.49
[58] Field of Search .................... 435/7.21, 29, 2; 436/501; 514/21; 424/1.49

[56] References Cited

U.S. PATENT DOCUMENTS

| | | | |
|---|---|---|---|
| 4,675,392 | 6/1987 | Dahmen | 536/17.6 |
| 4,683,213 | 7/1987 | Ax | 436/501 |
| 4,713,975 | 12/1987 | Tomalia et al. | 73/865.8 |
| 4,767,703 | 8/1988 | Ax et al. | 435/29 |
| 5,109,126 | 4/1992 | Agrawal et al. | 536/26.23 |
| 5,250,417 | 10/1993 | Feuchter | 435/23 |
| 5,256,539 | 10/1993 | Bronson | 435/7.21 |
| 5,338,532 | 8/1994 | Tomalia et al. | 424/1.49 |
| 5,389,519 | 2/1995 | Bronson | 435/7.21 |
| 5,434,139 | 7/1995 | Ax et al. | 514/21 |

FOREIGN PATENT DOCUMENTS 1249501  1/1989  Canada.

OTHER PUBLICATIONS

Benoff et al (Human Reprod.) vol. 8(12), pp. 2141–2154, 1993.
Mori, K et al (Am. J. Obstet. Gynocol.), vol. 161, pp. 207–211, 1989.
Sinowatz, F et al. (Histochemistry), vol. 88, pp. 395–399, 1988.
Silverberg, KM et al. Am. Fert. Soc., Abs. #0118, Montreal, Oct. 11–14, 1993.
Rogers, BJ et al. Bio. of Reprod., vol. 43, pp. 1064–1069, 1990.
Tulsiani, et al. J of Cell Biology, vol. 109, Sep. pp. 1257–1267, 1989.
Tulsiani, DRP et al. 6th Int. Congress of Spermatology. Aug. 30–Sep. 5, 1990, vol. 75, Raven Press, 1991.
Tesarik et al, Fertil Steril, vol. 56, 113, 1991.
Jones, R et al. Development, vol. 102, pp. 781–792, 1988.
Macek, MB et al. Gamete Research, vol. 20, pp. 93–109, 1988.
Nardone, P et al. Am. J. Reprod. Immunol, vol. 19(4) pp. 124–128, 1985.
Ravnik, SE et al. Fert. & Steril, vol. 59(3), Mar. pp. 629–638, 1993.
de Cerezo, JMS et al. J. of Reprod. Immun., vol. 14, pp. 213–223, 1988.
Holden, CA et al. Mol. Reprod. & Dev., vol. 25, pp. 247–257, 1990.
Hoodbhoy, T et al. Mol. Reprod & Dev., vol. 39, pp. 439–448, 1994.
Jones, R., Development, vol. 111, pp. 1155–1163, 1991.
Silverberg, KM et al. Soc. Gynecolog. Invest., 40th Annual Meeting, Mar. 31–Apr. 3, Toronto, CA, p. 369, # p. 374, 1993.
Ax, RL et al. J. Dairy Sci. vol. 70, pp. 1477–1486, 1987.
Ax, RL et al. J. Dairy Sci. vol. 68, pp. 387–390, 1985.
Cohen–Dayag. et al, Am. Physiology–Society, Am. J. Physiol, Cell Physiolog, vol. 267 (5), C1167–C1176, 1994.
Brandelli, et al., Biochim. Biophys. Acta, 1220:299–304 (1994).
Silverberg, Amer. Fertil. Soc. Meeting conjointly with the Canadian Fertil and Androl. Soc., Abs. 0–118, Montreal, Oct. 11–14 (1993).
Gilbert, Amer. Fertil. Soc. Meeting conjointly with the Canadian Fertil. and Androl. Soc., Abs. 0–161, Montreal, Oct. 11–14 (1993).
P. Sailing, "Mammalian sperm interaction with extracellular matrices of the egg" In: *Oxford Reviews of Reproductive Biology*, Oxford (New York), 1989.
Benoff et al., Hum. Reprod. 8:2155–2166 (1993).
Benoff et al., Hum. Reprod. 8:2141–2154 (1993).
Tomalia et al., Polymer Journal 17:117–132 (1985).
Tomalia et al., Macromolecules, 19:2466–68 (1986).
Cross et al., Biol. Reprod., 38:235–242 (1988).
Fraser, Methods Enzymol., 225:239–253 (1993).
Storey, Ann. NY Acad. Sci., 637:459–473 (1991).
Cross et al., Gam. Res., 15:213–226 (1986).
Miller et al., Development, 118:1279–1288 (1993).

(List continued on next page.)

Primary Examiner—James C. Housel
Assistant Examiner—Ginny Allen Portner
Attorney, Agent, or Firm—Lerner, David, Littenberg, Krumholz & Mentlik

[57] ABSTRACT

A method of evaluating the in vitro or in vivo fertilization capability of a given sperm sample. The method involves the steps of capacitating a sample of mammalian sperm cells followed by incubating the capacitated sperm with a predetermined amount of a glycoside-macromolecule conjugate such as a neoglycoprotein or a glycodendrimer for a period of time and under conditions sufficient to induce an acrosome reaction in the sperm. This step effectively mimics the physiological reaction that occurs in vivo between a sperm and an egg. The extent of the conjugate-induced acrosome reaction in the sperm cells relative to a positive control and a negative control, which account for the percent of sperm in the sample that acrosome react non-physiologically and spontaneously, respectively, is then calculated. The fertilization capability of the sperm is then evaluated as a function of the extent of this calculation. Also disclosed are kits which contain the necessary materials for conducting the method in a clinical laboratory.

19 Claims, No Drawings

OTHER PUBLICATIONS

Tesarik et al., Fertil. Steril., 60(2):344 (1993).
Benoff et al., Fertil. Steril. 59:854–862 (1993).
Smith et al., J. Biol. Chem., 255(1):55–59 (1980).
Sando et al., Biochemistry, 19(16):3850–3855 (1980).
Karson et al., Biochemistry 19(16):3856–3860 (1980).
Mori et al., Amer. J. Obstet. Gynecol., 161:207–211 (1989).
Godknecht et al., Dev. Biol., 143:398–407 (1991).
Mahony et al., Contraception, 44:657–665 (1991).
Oehniger et al., Fertil. Steril., 55:165–169 (1991).
Franken et al., Fertil. Steril., 59:1075–1080 (1993).
Liu et al., Fertil. Steril., 58:465–483 (1992).
Cummins et al., J. Androl., 12:98–103 (1991).
Tesarik et al., FEBS Lett., 308:116–120 (1992).
Kumar et al., Andrologia, 22:184–194 (1990).
Valz–Gianinet et al., Dev. Biol. 146:422 (1991).
Atnip et al., J. Exp. Zool., 243(3):461–472 (1987) (Abstract only).
Nishikawa et al., Int. J. Pharm (AMST) 85(1–3):75–85 (1992) (Abstract only).
Konno et al., Exp. Hematol. 18(3):185–189 (1990).
D. Mortimer et al., The Spontaneous Acrosome Reaction of Human Spermatozoa Incubated *in vitro*, Human Rep. 4(1):57–62 Jan. 1989.
D.R. Tulsiani, et al., Human Sperm Plasma Membranes Possess D–Mannosidase Activity But No Golactosyltransferase Activity, Bio of Rep 42:843–858 (1990).
Brandelli et al., "Aggregation of Binding Sites for N–Acetylglucosamine Residues Induces Acrosomal Exocitosis in Human Sperm," in Society for the Study of Reproduction, Aug. 1–4, 1993.

INDUCTION OF THE ACROSOME REACTION TO EVALUATE THE FERTILIZATION CAPABILITY OF MAMMALIAN SPERM USING A DENDRIMER SUGAR CONJUGATE

This is a continuation of application Ser. No. 08/213,195 filed Mar. 14, 1994 now abandoned.

BACKGROUND OF THE INVENTION

The advent of in vitro fertilization (IVF) has enhanced the value of methods that predict sperm fertilization capability of sperm to be used in such IVF treatment. Classical semen analysis, including sperm concentration, motility and morphology, is widely used as a primary indicator of male fertility. However, these results do not provide precise diagnostic or prognostic information for human fertility in vivo or in vitro. Because standard semen analysis has been demonstrated to have limited clinical value for predicting fertility, many other tests of human sperm function have emerged. These include an objective assessment of motility, hypo-osmotic swelling, tests for sperm nuclear maturity, measurements of acrosome status, acrosome reaction and acrosine activity, hamster zona-free oocyte penetration, and human sperm-zona binding and penetration.

The use of living human oocytes for testing human sperm function has proved virtually impossible due to the limited amount of the test material. The currently most popular test, the zona-free hamster ovum sperm penetration assay SPA, assesses the ability of human sperm to capacitate, acrosome react, fuse with the oolemma, and undergo decondensation in the cytoplasm. R. Yanagimachi, Biol. Reprod. 15:471–76 (1976). However, this test has several limitations because it does not measure the ability of the sperm to bind to and penetrate the zona pellucida (ZP). The test is also deficient in that it does not reflect the behavior of the whole sperm population. For example, a small fraction of acrosome-reacted sperm may be responsible for fusion with all of the oocytes used in the assay. Further, this test cannot predict infertility due to failure of the sperm to penetrate the ZP. Others have criticized this test on the basis of evidence demonstrating a relatively poor correlation between sperm penetration of the sperm with the hamster oocyte versus that with the human oocyte. Takahashi et al., Fertil. Steril. 57(4):889–894 (1992).

Other tests such as the hemizona assay (HZA) utilize parts of zonii from human oocytes. Burkman et al., Fertil. Steril. 49:688–97 (1988). Positive correlations between the sperm-ZP binding index obtained by the HZA and IVF have been reported. See Franken et al., J. In Vitro Fert. Embryo Transf. 6:44–50 (1989) and Oehninger et al., Fertil. Steril. 51:665–70 (1989). However, the HZA has been criticized, for among other reasons, because the large variation in the results makes the test unsuitable for routine use in the assessment of all infertile men. See Liu et al., Fertil. Steril. 58(3):465–484 (1992).

Tests such as the HZA which require portions of the ZP of fresh mature human oocytes are further impractical because they are dependent on the availability of sufficient quantities of fresh or stored human ZP from oocytes that are a byproduct of IVF programs. If this material is used, only very few tests can be performed, and only in labs associated with IVF programs. Moreover, oocytes obtained from cadavers are of dubious quality. The poorly controllable nature of these factors has underscored the interest in replacing this biological material with defined chemical compounds that mimic the sperm binding sites on the ZP. See Tesarik et al., Fertil. Steril. 60(2):344–350 (1993).

The acrosome reaction is known to be critical for fertilization, and several assays which test this function have been developed. However, the measurement of the acrosome reaction alone is not reliable per se. For example, Cummins et al., J. Androl. 12(2):98–103 (1991), discloses a test of the human sperm acrosome reaction following calcium ionophore challenge. This method, however, is unable to distinguish live from dead sperm, nor does it give any information on the ability of the sperm to fuse with an exposed oocyte surface. Id. It has been further proposed to study the kinetics of the acrosome reaction in vitro to predict sperm fertilizing ability. Topfer-Petersen et al., Andrologia 17:224–27 (1985). A positive correlation between spontaneous acrosome exocytosis and IVF has been reported in Benoff et al., Hum. Reprod. 8(12):2155–2166 (1993). However, the results of other studies failed demonstrate a correlation between the ability of human sperm to undergo an acrosome reaction in culture medium and to fertilize oocytes in vitro. See, e.g., DeJonge et al., Fertil. Steril. 50:949–53 (1988).

Clearly, conventional semen analysis provides limited information about fertility, and must be supplemented with additional sperm function tests provide a more accurate prediction of in vitro or in vivo fertility. These efforts have been thwarted by an incomplete understanding about sperm characteristics and their relationship to the process of fertilization. Thus, a need remains not only for a highly accurate sperm fertilization capability test, but one which can be routinely performed in a clinical laboratory at low cost.

SUMMARY OF THE INVENTION

Disclosed is a method of evaluating the in vitro or in vivo fertilization capability of a given sperm sample. The method involves the steps of capacitating a sample of mammalian sperm cells followed by incubating the capacitated sperm with a predetermined amount of a glycoside-macromolecule conjugate such as a neoglycoprotein or a glycodendrimer for a period of time and under conditions sufficient to induce an acrosome reaction in the sperm. This step effectively mimics the physiological reaction that occurs in vivo between a sperm and an egg. The extent of the conjugate-induced acrosome reaction in the sperm cells relative to a positive control and a negative control, which account for the percent of sperm in the sample that acrosome react non-physiologically and spontaneously, respectively, is then calculated. The fertilization capability of the sperm is then evaluated as a function of this calculation.

Kits which contain the materials for conducting the method in a clinical laboratory are also encompassed by the present invention.

DESCRIPTION OF THE PREFERRED EMBODIMENTS

Following ejaculation, there are two critical changes in sperm that must occur before they can fertilize an egg. The first event is the capacitation of sperm cells. Capacitation is generally understood by those skilled in the art to mean the complex of ultrastructural and biochemical changes that occur in sperm that enable the sperm to undergo an acrosome reaction. Yanagimachi, "Mammalian Fertilization," In *The Physiology of Reproduction*, Knobil et al. (eds.), Raven (N.Y.) 1988, at pages 135–185; P. Saling, "Mammalian sperm interaction with extracellular matrices of the egg," In: *Oxford Reviews of Reproductive Biology*, Oxford (N.Y.), 1989; and Takahashi et al., Fertil. Steril. 57(4):889–894 (1992). For example, it has been demonstrated in animals that the expression of sperm membrane proteins (zona pellucida receptors) that recognize specific glycoconjugate ligands on the zona pellucida are masked in freshly ejaculated sperm so that sperm cannot bind to the zona pellucida and cause fertilization. Through the process of capacitation, these receptors are exposed so that the sperm can then bind to the zona pellucida. Macek et al., Gam. Res. 20:93–109 (1988); Leyton et al., J. Cell Biol. 108:2163–68 (1989), and Beebe et al., Dev. Biol. 151:48–54 (1992).

The second event is the subsequent acrosome reaction that occurs when the capacitated sperm binds to the zona pellucida of the oocyte. The acrosome reaction is generally understood by those skilled in the art to mean a multi-step physiological process that is induced in vivo when a capacitated sperm cell binds to the extracellular coat of the egg, i.e., the zona pellucida (ZP). The acrosome reaction is characterized by the ligand-mediated aggregation of the ZP receptors on the sperm membrane, an influx of calcium ions into the sperm, fusion of the outer acrosomal membrane to the sperm plasma membrane, and the concomitant release of acrosomal enzymes via pores formed in the fused membranes. See P. Saling, supra.

Although there is fragmentary evidence suggesting that analogous processes occur in man, no study has conclusively established the molecular nature of human sperm zona binding proteins. In addition, much of the research directed at determining the receptors on the human sperm surface that mediate zona pellucida recognition has been thwarted by the limited availability of human oocytes required for such detailed studies. Id.

Notwithstanding the prevailing uncertainty and unpredictability regarding the nature of the acrosome reaction between human gametes, applicants have surprisingly and unexpectedly discovered that the ligand-mediated acrosome reaction that occurs when capacitated sperm and oocytes come into contact with each other in vivo can be effectively reproduced in vitro without using whole oocytes, ZP or any other naturally occurring, acrosome-inducing biological material, by incubating a given capacitated sperm cell sample with a conjugate of a glycosidic derivative of a sugar and a macromolecule (hereinafter "glycoside-macromolecule conjugate"). The extent of the conjugate-induced acrosome reaction in the given sperm sample is measured, and then expressed or calculated relative to the positive and negative control results. In turn, this relative value is used to accurately assess the in vivo or in vitro fertilization capacity of the sperm of the male from which the sample was obtained. That is, the method of the present invention can be used to accurately predict in in vitro fertilization capability of a given male patient enrolled in an In Vitro Fertilization (IVF) program, as well as to determine the etiology of any infertility.

Using the neoglycoprotein FITC-mannose-BSA (fluorescein isothiocyanate mannose bovine serum albumin) and the binding inhibitor mannose-BSA, a positive correlation between the presence of mannose receptors on sperm and fertilization potential in vitro has been demonstrated. See Benoff et al., Hum. Reprod. 8(12):2155–66 (1993). However, these binding assays are significantly less accurate than the method of the present invention in terms of predicting fertilization capability. Because the labeled conjugates are used merely to identify the mannose binding sites but not to induce the acrosome reaction in the sperm, these assays fail to test the functionality or viability of all the cellular mechanisms involved in the acrosome reaction. For instance, binding of sperm receptors to the ZP is the first step in the acrosome reaction, yet it is not in and of itself determinative as to whether the acrosome reaction and fertilization of the egg will occur.

The so-called "induction" of the acrosome reaction by 75 mM free mannose is reported in Benoff et al., supra, and in the companion publication, Benoff et al., Hum. Reprod. 8(12):2141–2154 (1993). However, in sharp contrast to the method of the present invention, treatment of sperm with 75 mM mannose induces a drastic non-physiological, e.g., pharmacological, effect on the sperm. This results in increased acrosome exocytosis, but it is not physiologically induced, i.e., mediated by the ligand-mediated aggregation of ZP receptors on the sperm membrane (P. Saling, supra.). This difference is highly significant for the same reason set forth above in that induction with 75 mM mannose simply does not test the functionality of the cellular mechanisms involved in the acrosome reaction that occurs in vivo. Thus, prior to Applicant's invention, the prior art had simply failed to consider or appreciate that various neoglycoproteins could be used to induce an acrosome reaction in capacitated sperm as part of an assay to accurately predict the fertilization capability of a male.

To conduct the method of the present invention, it is first necessary to obtain a sperm sample. Sperm samples may be collected and then subjected to routine analysis for such parameters as volume, concentration, average grade of velocity, and percentage of motile cells, in accordance with standard procedures. See, e.g., World Health Organization, *WHO Laboratory Manual for the Examination of Human Semen and Semen-Cervical Mucus Interaction*, 3rd Ed., Cambridge (1992) (hereinafter "The WHO Laboratory Manual").

The thus-obtained sperm sample is then capacitated in accordance with methods known in the art. See, e.g., Bedford, Biol. Reprod. 25:108–120 (1983); Bellvé et al., Meth. Enzymol. 225:113–136 (1993); Calvo et al., Hum. Reprod. 8:575–580 (1993) and Fertil. Steril. 52:1048–1054 (1989); Fraser, L.R., Arch. Pathol. Lab. Med. 116:345–350 (1992) and Meth. Enzymol. 225:239–253 (1993); Storey, Ann. NY Acad. Sci. 637:459–473 (1991); Stovall et al., Fertil. Steril. 56:960–966 (1991); Zaneveld et al., Hum. Reprod. 6:1265–1274 (1991); Tesarik et al., Development 110:391–400 (1990); and Tesarik et al., FEBS Lett. 308(2) :116–120 (1992). In general, capacitation of any given sperm cell sample is achieved by incubating the sample for about 16 hours at about 37° C. in culture medium containing of from about 3–20 mg/ml of bovine serum albumin or an equivalent substance, and equilibrated with about 5% $CO_2$. A preferred capacitation protocol is set forth in the *WHO Laboratory Manual*. These operating parameters take into account the fact that sperm from different individuals may capacitate at different rates. Perrault et al., Fertil. Steril 38:258–60 (1982). In general, sperm concentrations range from about $1.0 \times 10^6$ to about $1.0 \times 10^7$ cells/ml of medium. Preferred sperm concentrations are in the range of from about $2.0 \times 10^6$ to about $3.0 \times 10^6$ cells/ml of medium.

The thus-capacitated sperm cells are incubated with a predetermined concentration of a glycoside-macromolecule conjugate under conditions, e.g., temperature and period of time, sufficient to induce an acrosome reaction in the capacitated sperm. Glycosides are the reaction products of aldopyranoses and alcohols. See Chapter 10 in Lehninger, *Biochemistry*, Worth (1975). Representative sugar moieties of the glycosides include N-Acetyl-β-D-glucosamine (GlcNAc), also known as 2-acetamido-2-deoxy-D-glucosamine, N-Acetyl-β-D-galactosamine, and mannose.

GlcNAc and mannose are preferred. However, as further explained hereinbelow, other sugars are operable in the present invention. The N-ε-aminocaproyl, p-isothiocyanatophenyl and p-aminophenyl glycosides of these sugars are preferred. However, those skilled in the art will appreciate that any other glycosidic groups which are capable of functioning as a stable linkage group between the sugar and the macromolecule, can be used in the present invention. In general, the concentration of the conjugate is in the range of from about 0.6 µg/ml to about 3.0 µg/ml of medium. The preferred range is from about 1 µg/ml to about 2 µg/ml. The more preferred concentration is about 1 µg/ml.

The macromolecule can be any natural or synthetic globular polymeric material capable of functioning as a carrier molecule for the derivatized sugar, and which is inert to the sperm cells. That is, the macromolecule lacks sugar residues that could potentially interfere with the acrosome reaction, or it can be chemically pretreated, e.g., with sodium periodate, to remove native sugar residues. Examples of synthetic materials include derivatizable amino group-containing polymers such as polylysine, polyasparagine, polyarginine, and dendrimers capable of being coupled to the glycosides. Dendrimers are polyamidoamines having an ammonia initiator core which undergoes an alkylation reaction followed by amidation to complete monomer addition. Several repetitions of this process yield a macromolecule with monodisperse amino groups in the exterior. Dendrimers can be obtained from known sources, e.g., Starburst™ (Dow Chemical Co.). In the alternative, they can be synthesized in accordance with standard procedures. See Tomalia et al., Polymer J. 17:117–132 (1985) and Tomalia et al., Macromolecules 19,266 (1980). Suitable natural polymeric materials include proteins such as serum globulins, e.g., albumins (bovine serum albumin (BSA), human albumin, and ovalbumin) and other known proteinaceous carriers such as transferrin and keyhole limpet hemocyanin. Macromolecules having a molecular weight greater than about 10,000 Da are preferred.

Methods for preparing glycoside-protein conjugates, commonly referred to as neoglycoproteins, are known in the art. See, for example, Monsigny et al., Biol. Cell. 51:187–196 (1984); Sando et al., Biochem. 19(16):3850–3855 (1980) (disclosing synthetic schemes for the p-aminophenyl and p-isothiocyanatophenyl glycosides of various sugars); Karson et al., Biochem. 19(16):3856–60 (1980); and Smith et al., J. Biol. Chem. 255(1):55–59 (1980). These methods are equally applicable in the case where the macromolecule is synthetic.

Preferred glycoside-macromolecule conjugates are N-acetyl-β-D-glucosamine phenylisothiocyanate BSA, para-aminophenyl-N-acetyl-β-D-glucosaminide-BSA (BSA-GlcNAc), and p-aminophenyl-α-D-mannopyranoside-BSA (BSA-Man). BSA-GlcNAc and BSA-Man are more preferred.

In general, the conditions for the induction of the acrosome reaction in the capacitated sperm by the glycoside-macromolecule conjugate are substantially the same as the conditions used to induce the acrosome reaction by zoha pellucida, see, for example, Cross et al., Biol. Reprod. 38:235–242 (1988). Not all sperm in any given induced sperm sample are capable of undergoing the acrosome reaction. That is, a certain percent are refractory to the reaction. Thus, the incubation should be continued for a period of time sufficient to complete the reaction, i.e., to induce an acrosome reaction in the maximum number of the sperm in the sample which are capable of undergoing the conjugate-induced acrosome reaction. Those skilled in the art will appreciate that this period of time can be determined in accordance with standard procedures such as time course studies. The incubation should preferably be conducted for at least about 1 hour. Shorter incubation time periods, e.g., 15 minutes, have been disclosed for the purpose of conducting binding assays. See Benoff et al., Fertil. Steril. 59(4):854–62 (1993) and Benoff et al., Hum. Reprod. 8(12):2141–2154 (1993). However, since this time period would cause less than about 40% of the sperm to undergo the conjugate-induced acrosome reaction, it underscores the distinct and unrelated purpose of these prior art methods. In an even more preferred embodiment, the capacitated sperm cells are incubated with the glycoside-macromolecule conjugate for about 1 hour at 37° C. in an atmosphere of air and 5% $CO_2$.

Upon completion of the acrosome reaction, the sperm are isolated from the incubation medium and analyzed individually to determine the number of cells in the sample that have undergone the acrosome reaction. Those skilled in the art can perform this analysis according to standard microscopic techniques using a variety of reagents such as the triple stain, monoclonal antibodies to acrosomal components, chlorotetracycline fluorescence, and fluorescein isothiocyanate (FITC)-labelled lectins, e.g., Pisum sativum agglutinin (PSA) and peanut agglutinin. See Liu et al. supra., and references cited therein. Electron microscopy is generally considered as the most effective method for assessing acrosomes, but it is not practical for routine use because the technique is expensive and time consuming. Methods using detectable labels as described above are generally preferred for use in the clinical laboratory. Those skilled in the art would be able to select the appropriate method for their purposes. See Cross et al., Biol. Reprod. 41:635–41 (1987).

Pisum sativum agglutinin fluorescein stains are preferred because they provide a simple and reproducible technique for the routine assessment of human acrosomes. Mendoza et al., J. Reprod. Fertil. 95:755–763 (1992); Liu et al., Fertil. Steril. 50:288–93 (1988). A supravital stain, e.g., Hoechst 33258 (Sigma Chemical Co., St. Louis, Mo.), or hypo-osmotic swelling in conjunction with the PSA acrosome assessment will allow those skilled in the art to differentiate living and dead acrosomeless sperm. Cross et al., Gam. Res. 15:213–226 (1986). Acrosome analysis can also be conducted using Pisum sativum agglutinin coupled to dyed latex microparticles (e.g., 0.2 microns, Polyscience Inc. or Interfacial Dynamics Corp.), in which case standard light microscopes may be used. The extent of the acrosome reaction can also be determined by fluorescence-activated cell sorting using flow cytometry devices. See, for example, Tesarik et al., Fertil. Steril. 58:784–92 (1992).

In accordance with the present invention, at least one control assay is performed on an aliquot of the sperm sample. This assay tests the capacity of the sperm to undergo the acrosome reaction non-physiologically, i.e., independent of their ability to bind to the ZP and undergo ligand-dependent aggregation of sperm receptors, as well as to more generally identify patients whose infertility is due to mechanistically distinct reasons. See Liu et al., Fertil. Steril. 58(3):465–483 (1992) and references cited therein. To conduct the positive control, the acrosome reaction is induced by a non-natural, e.g., synthetic, acrosome-inducing substance such as a chemical. As in the case of the conjugate-induced acrosome reaction, the positive control assay should be run to completion to maximize the accuracy of the instant method. Those skilled in the art will be able to determine optimal reaction conditions in accordance with standard procedures. Calcium ionophore A23187 and ionomycin (Sigma Co., St. Louis), which are reportedly believed to induce the acrosome reaction non-physiologically, are preferred. Tesarik et al., J. Reprod. Fertil. 74:383–88 (1985); Cummins et al., J. Androl. 12(2):98–103 (1991). In general, the concentration of ionophore is from about 5 to about micromolar. The preferred concentration is about 10 micromolar.

A second, negative control assay is performed on an aliquot of the sperm sample using a medium or buffer solution that does not contain an acrosome reaction-inducing material. This assay is conducted to determine the percent of sperm in a given sample which undergoes the acrosome reaction spontaneously under test or assay conditions. That is, it measures the relatively small percentage of sperm cells in any given sperm sample that will undergo the acrosome reaction regardless of the presence of an acrosome reaction-inducing substance. Thus, this assay further enhances the accuracy and reliability of the instantly disclosed method. The extent of the acrosome reaction in each of the positive and negative controls can be measured in accordance with the methods described above.

The negative control assay also provides a means by which glycosides other than those specifically described above can be used in the method of the present invention. Specifically, any such glycoside, which when coupled to the macromolecule (as described above) causes at least a two-fold increase in stimulation of the acrosome reaction compared to the negative control (as the term is used herein), is suitable for use in the present invention.

The extent of the conjugate-induced acrosome reaction is then calculated relative to the results of the positive and negative controls. In a preferred embodiment, this value is expressed as a percentage of relative stimulation (% STIM). The relative stimulation is the difference in the extent of the acrosome reaction between the conjugate-induced sperm cells and the negative control, i.e., spontaneously induced sperm cells, divided by the difference in the extent of the acrosome reaction between the positive control, i.e., the non-physiologically induced sperm, and the negative control.

The calculation of the relative extent of the acrosome reaction is then used to evaluate or determine the fertilization capability of the sperm from the male in accordance with methods known in the art. In a preferred embodiment, the individual results obtained from sperm samples from several patients are correlated with the capability of the same sperm sample to fertilize oocytes from fertile female egg donors in vitro and then accumulated. Such a correlation based upon accumulated patient data will allow one skilled in the art to establish a STIM range corresponding to normal and abnormal fertilization rates, and thus accurately predict the fertilization capability of the sperm of a given male.

The disclosed method effectively overcomes the many difficulties associated with currently available fertilization tests. It does not rely on or require human or animal ova, ZP, follicular fluid or any other natural biological composition. It can be performed with reagents that are readily available and easy to synthesize. In addition, the results of the test are highly reproducible. The method provides more reliable statistical information on the given sperm population of a male because the spermatozoa are scored on an individual basis. Further, in view of the aforementioned advantages, the method more accurately predicts when the etiology of infertility involves a defect in the spermatozoa per se, and thus will obviate the need for further evaluation and treatment which often involves expensive surgical procedures.

Moreover, while the use of human sperm is preferred, the method of the present invention is applicable to other mammalian species as well.

The method of the present invention can be easily performed in clinical laboratories. To facilitate this use, kits containing the necessary reagents to conduct the method are also provided by the present invention. In general, the kits comprise pre-made solutions of the glycoside-macromolecule conjugate, and the detectable label. They also comprise individual solutions of the positive control and the negative control. For example, solutions of the glycoside-macromolecule conjugate and the positive and negative controls can be added to separate assay containers, dried under a stream of nitrogen, and capped. These solutions will remain viable for about 6 months when stored under refrigerated conditions. In the event that the acrosome reaction determination is conducted microscopically, the kits may further contain one or more mounting devices, e.g., microscope slides, upon which to conduct the measurement of the acrosome reacted sperm.

The invention will be further described by reference to the following detailed examples. These examples are provided for purposes of illustration only, and are not intended to be limiting unless otherwise specified. Unless otherwise indicated, all percentages are by weight.

EXAMPLES

Example 1

Preparation of Neoglycoproteins

Para-aminophenyl-N-acetyl-β-D-glucosaminide-bovine serum albumin ("BSA-GlcNAc"), para-aminophenyl-N-acetyl-β-D-galactosaminide-bovine serum albumin ("BSA-GalNAc"), and para-aminophenyl-α-D-mannopyranoside-bovine serum albumin (BSA-Man) were obtained from Sigma Chemical Co. (St. Louis, Mo.). Pyranosylphenyl-isothiocyanate derivatives of fucose, galactose, glucose and lactose and N-acetyl-β-D-glucosamine phenyl isothiocyanate were also obtained from Sigma, and were coupled to BSA as described in Monsigny et al., Biol. Cell. 51:187–196 (1984). This technique was also used to derivatize BSA with the two residues N-acetyl-β-D-glucosamine-phenylisothiocyanate and mannosephenylisothiocyanate. These residues were dissolved at 10 mg/ml concentration in 0.1M sodium carbonate buffer at a pH of 9.5, and were mixed with 10 volumes of BSA at a concentration of 1 mg/ml in the same buffer. The incubation was allowed to proceed overnight at 5° C. The reaction was stopped by the addition of 300 ul of 0.5M ethanolamine in PBS, followed by incubation for 30 minutes at room temperature. The derivatized BSA was separated from nonreacted sugars by chromatography on Sephadex™ G-25.

Example 2

Preparation of Glycoside-Dendrimer Conjugates

Multiple residues of the glycoside N-Acetyl-B-D-glucosamine phenylisothiocyanate were coupled to polyamidoamine dendrimer microparticles (Starburst™, Dow Chemical Co.) as follows. Dendrimer Starburst™ (Polyscience catalog #21153) are particles having a diameter of 40 Angstroms and a molecular weight of 43,500. They carry 192 $NH_2$ residues per molecule. Stock solutions provided by the manufacturer have a concentration of $2 \times 10^{16}$ molecules per ml or 33 mM. Dendrimer stock solution (1 ml) was supplemented with 0.15 ml of 0.5M sodium carbonate (pH 9.5) and 0.5 mg of N-Acetyl-β-D-glucosamine phenyl isothiocyanate dissolved in 200-ul a mixture of water and dimethylsulphoxide (1:1). The incubation was allowed to proceed overnight at 5° C. The reaction was stopped by the addition of 300 ul of 0.5M ethanolamine in PBS followed by incubation by 30 minutes at room temperature. The derivatized dendrimers were separated chromatographically from other reagents by passage through a column of Sephadex™ G-25 equilibrated in distilled water. The same protocol was used for coupling of mannose phenylisothiocyanate. The rate of incorporation in the eluate of the Sephadex column was evaluated by spectophotometry between 200 and 320 nm. The coupled residues present a characteristic of absorbance peak at 240 nm. Using this coupling protocol, half maximal incorporation of glycoside residues was achieved, thus assuring that the dendrimer conjugates were functionally equivalent to the GlcNAc-BSA for purposes of the disclosed method.

Example 3
Preparation of Semen Samples and Sperm Capacitation

Semen samples were obtained from fertile men according to World Health Organization standards. See the *WHO Laboratory Manual*, supra. After complete liquefaction, sperm cells were separated from seminal plasma on a 50% isotonic Percoll™ gradient by layering one half milliliter of each sample onto 700 µl of Percoll™ in 1.5 ml microcentrifuge conical tubes and centrifuging for 10 min at 900× g. The sperm pellet was resuspended and washed twice in BWW medium, Biggers et al., *Methods in Mammalian Embryology*, Freeman (San Francisco), 1978 at pp. 86–116, (containing 35 mg/ml BSA, fraction V (a standard fractionation of serum, of which the major component is albumin; available from Sigma Chemical Co.) by spinning at 900× g in a conical 1.5 ml tube in a microcentrifuge. The final pellet was resuspended and washed twice in BWW medium ($5\times10^6$ cells/ml) and incubated in similar tubes for 10 to 18 hours at 37° C. and 5% $CO_2$ in air.

Example 4
Induction of the Acrosome Reaction

Following capacitation, aliquots (300–400 ul) of the sperm suspension ($1-2\times10^6$ cells/ml) were transferred to plastic microcentrifuge tubes. The following solutions were added: A) 20 ul fresh BWW medium as a negative control; B) 20 ug of a stock solution of 200 ug/ml each of the different glycoside-macromolecule conjugates prepared in Examples 1 and 2 (1–2 ug/ml final concentration); and C) 2 ul of a stock solution of 1 mM calcium ionophore A23187 (Calbiochem-Behring, San Diego) in dimethylsulfoxide, or ionomycin at a final concentration of 10 µM as a positive Control. The tubes were capped and then stirred for a few seconds. The tubes were then opened and incubated for 60 minutes at 37° C. in an atmosphere of 5% $CO_2$ in air.

Example 5a
Measurement of Acrosome Reaction Fluorescently

The measurement of the acrosome reaction was conducted according to the method described in Cross et al., Gam. Res. 15:213–226 (1986), with minor modifications as disclosed in Mendoza et al., J. Reprod. Fertil., 9.5:755–763 (1992). After treatment with the neoglycoproteins or buffer, the sperm cells were washed three times by centrifugation in PBS (1 ml each time), and plated onto polylysine-coated slides in a humid chamber. After cells adhered to the surface (approximately 20 min), the buffer was removed with a pipette, the cells were allowed to dry for 2 min, and the slides were submerged in 95% methanol for 30 sec at 4° C. for cell permeabilization, followed by rapid drying under a stream of air at room temperature. Polylysine coating of slides was performed by drying 30 ul of a solution of 0.02 mg/ml polylysine (MW 15,000, Sigma Chemical Co., St. Louis, Mo.) on fluorescence slides (Polyscience, Warrington, Pa.. These slides were kept in a dust-free, sealed plastic envelope or box in the cold, e.g., 5°–10° C., until use.

The slides were dried at room temperature, and each well was incubated with 30 ul of 50 µg/ml *pisum sativum* agglutinin coupled to fluorescein isothiocyanate (FITC) in phosphate buffer saline solution, 20 mM sodium phosphate, 0.15 M sodium chloride pH 7.2 (PBS), for 30 min. at room temperature. The unbound lectin was removed by washing the slides with a stream of distilled water and submerging them in water for 15 min. at room temperature. The slides were then dried under a stream of air at room temperature and mounted in a mixture of PBS:glycerol (1:9 weight ratio) and covered with coverslips. Fluorescent cells were scored in an epifluorescence microscope equipped with a fluorescein filter (Labophot microscope, Nikon, Nippon Kogaku K. K., Japan). One hundred cells were scored per well for the different staining status as disclosed in Cross et al., and Mendoza et al., supra.

The results were expressed as the percentage of relative stimulation;

$$\% \, STIM = \frac{\% \, ARt - \% \, ARc}{\% \, ARi - \% \, ARc} \times 100$$

wherein % ARt represents the percentage of acrosome reaction (AR) in treated cells, % ARc represents the percentage of AR in cells incubated only in buffer (negative control), and % ARi represents the percentage of AR in ionophore-treated cells (positive control). Examples of these three values each for a normal (fertile) and infertile man are shown on lines 2, 1 and 3, respectively, in Table 1 below.

Example 5b
Measurement of Acrosome Reaction Non-Fluorescently

The acrosome of sperm were capacitated in accordance with the procedure described in Example 3, and then stained with peroxidase-labelled *Pissum sativum* agglutinin (Vector, Burlingame, Calif.) at 1:100 dilution in PBS of 1 mg/ml stock solution according to the procedure described in Example 5a. After the incubation (60 min), the unbound lectin was washed with PBS and the peroxidase was visualized after reaction with 0.01% hydrogen peroxide and 0.04% diaminobenzidine in 0.1M Tris buffer, pH 7.2, for approximately 10 min.

Labelled sperm cells were scored using a standard light microscope (data not shown).

Example 6
Correlation of STIM Results and IVF Outcome in a Two-Patient Study

Spermatozoa from two patients (denoted A and B) participating an In Vitro Fertilization (IVF) protocol were analyzed in accordance with the method of the present invention simultaneously with the In Vitro Fertilization of their wives' oocytes. The spermatozoa from the patients were capacitated in BWW medium or equivalent without serum for 8–16 hours (first incubation), and then were transferred to a Petri dish with the human oocytes for fertilization. After 16 hrs, the 6 oocytes for Patient A and the 5 oocytes for Patient B were scored by observing decondensed sperm heads in the cytoplasm and emission of the second polar body. Aliquots of the first incubation, prior to the incubation with the oocytes, were supplemented with buffer, BSA-GlcNAc or ionophore as described in Example 4 and the acrosome reaction was measured as described in Example 5a.

The results are set forth below in Table 1.

TABLE 1

ACROSOME REACTION, STIM VALUES AND IN VITRO FERTILIZATION RESULTS IN TWO PATIENTS

| | Patient A | Patient B |
|---|---|---|
| INCUBATION | | |
| 1. Negative Control (% $AR_c$): | 10 ± 1 | 11 ± 2 |
| 2. BSA—GlcNAc (% $AR_t$): | 23 ± 3 | 14 ± 2 |
| 3. Ionophore (% $AR_i$): (Postive Control) | 31 ± 3 | 29 ± 2 |
| 4. % STIM: | 62% | 17% |
| 5. % IN VITRO FERTILIZATION | 100% | 0% |
| 6. Oocytes fertilized Oocytes analyzed | 6/6 | 0/5 |

The sperm from Patient A that had a normal STIM value of 62% (line 4) fertilized all of the human eggs used in the test (line 6). By contrast, the sperm from Patient B exhibited a low STIM value of 17% (line 4) and did not fertilize any of the human eggs (line 6).

By contrast, using the HOPT assay disclosed in the WHO Laboratory Manual, the spermatozoa from both patients A and B penetrated the hamster oocytes in the range considered normal, and thus gave an inaccurate result by failing to predict that the sperm from Patient B would not interact with and fertilize human eggs (line 6, table 1). Yet, sperm from patient B showed no binding to the human oocytes when they were exposed without the cumulus cell layers (denuded-zona intact oocytes).

The $AR_c$ values for Patients A and B (10±1% and 11±2%, respectively), which measures the percentage of the sperm in the sample that spontaneously acrosome react, comport with the measurements disclosed in FIG. 3(D) of Benoff et al., Hum. Reprod. 8(12):2155–66 (1993).

Example 7
Correlation of Mean STIM Values with IVF Results; Multi-Patient Study

Multiple follicular development was induced in women seeking treatment by IVF with a combination of follicle stimulating hormone (FSH) (Metrodine™: Serono Laboratories) and human menopausal gonadotrophins (HMG) (Pergonal™, Serono Laboratories). Oocyte retrieval was performed by vaginal ultrasound guided aspiration for 36 hours after a 5,000 IU HCG injection. Semen processing for IVF, oocyte insemination, and embryo culture as performed according to established guidelines as disclosed in Veeck et al., "Insemination and Fertilization," In In vitro Fertilization-Norfolk, Jones et al., (eds.), Williams and Wilkers (Baltimore), 1986 at p. 168.

Sperm from men of unknown fertility were capacitated in vitro as detailed above for 16 to 20 hours. An aliquot of 1 ml containing 1 to 2 million cells was used for the induction of the acrosome reaction with the glycoside-macromolecule conjugate and ionophore positive control.

Oocytes were examined for nuclear maturity immediately on collection by means of the "cumulus cell-spreading" technique and classified as immature (germinal vesicle present, Prophase I), Metaphase I (no germinal vesicle for first polar body present) or metaphase II (first polar body present).

Immature oocytes were maintained in culture in Ham F10 medium containing FSH for 24 hours until breakdown of the germinal vesicle occurred and then were incubated with spermatozoa for 16 to 24 hrs. Mature oocytes were inseminated either immediately upon retrieval or after culture in medium with equivalent results.

Each oocyte was inseminated with 10,000 to 100,000 spermatozoa per mililiter of Ham F 10 medium supplemented with 10 mg/ml of BSA. Twenty four hours after insemination, oocytes with two pronuclei were considered fertilized and were then cultured further with fresh fertilization medium for cleavage and replacement into women.

All the patients tested in accordance with the present invention previously to or simultaneously with the in vitro fertilization were grouped into two categories according to their rate of IVF: Group I had 0–25% of eggs that were fertilized, and was characterized as having a low fertilization rate; and Group II with 51–100% fertilized eggs was characterized as having a high fertilization rate.

The patients were grouped according to their performance in IVF (percent of oocytes fertilized). The cumulative results are set forth below in Table 2:

TABLE 2

| Group | No. Patients | % Eggs Fertilized | Mean % STIM | Stat. Diff. with Grp. 1 |
|---|---|---|---|---|
| 1 | 8 | 0–25% | 7 (±14) | — |
| 2 | 17 | 51–100% | 60 (±10) | ($P < 0.05$) |

All the patients tested were in those ranges for IVF either very low or very high. The statistical comparison of the results in the groups was made using the one-way variance test and Scheffe's test for multiple comparisons (STATGRAPHICS™, Graphic Software Corporation, Inc.) Two of the eight patients in Group 1 had relatively high STIM values (greater than 20%), yet had zero fertilization rates. These cases were carefully segregated. In these two cases, the failure to fertilize was due to a "female factor" rather than the sperm. This was detected by two approaches: a) no binding of sperm from fertile donors to the unfertilized oocytes, and b) fertilization when the sperm with the high STIM values were subsequently incubated with oocytes from fertile donors.

All the sperm samples with a STIM value lower than 15% fertilized zero to very few eggs. Thus, if sperm with normal STIM values do not fertilize an egg, the fertilizability of the oocyte must be investigated as the explanation of fertilization failure. This evaluation is performed by testing the fertilization of the unfertilized oocyte with sperm from fertile donors in accordance with standard techniques.

The results obtained with the method of the present invention have a positive correlation with IVF results. They are significantly more reliable than those obtained using known methods because they are based upon a comprehensive analysis of the capability of the sperm to undergo the acrosome reaction essential for fertilization, and not merely on one aspect thereof, e.g., binding. At the same time, the method avoids the various disadvantages associated with currently used methods. Further, as illustrated in Example 7, in the case where the sperm are fertile, the method allows for the detection of infertile eggs.

All publications and patent applications mentioned in the specification are indicative of the level of skill of those skilled in the art to which this invention pertains. All these publications and patent applications are herein incorporated by reference to the same extent as if each individual publication or patent application was specifically and individually indicated to be incorporated by reference.

Various modifications of the invention described herein will become apparent to those skilled in the art. Such what is claimed is:

1. A method for evaluating the fertilization capability of mammalian sperm cells, comprising the steps of:

capacitating s mammalian sperm cell sample;

incubating the thus-capacitated sperm cells with a conjugate of a dendrimer and a glycosidic derivative of a sugar under conditions suitable to induce an acrosome reaction in the capacitated sperm cells; and calculating the extent of the acrosome reaction in the thus-incubated sperm cells relative to a positive and a negative control, and evaluating the fertilization capability of the sperm cells as a function of the calculation.

2. The method of claim 1, further comprising reacting the thus-incubated sperm cells with a detectable label prior to said calculating the extent of the acrosome reaction.

3. The method of claim 1, wherein said sugar is N-acetyl-β-D-glucosamine.

4. The method of claim 1, wherein said sugar is N-acetyl-β-D-galactosamine.

5. The method of claim 1, wherein said sugar is mannose.

6. The method of claim 1, wherein said glycosidic derivative is p-aminophenyl-N-acetyl-β-D-glycosamide.

7. The method of claim 1, wherein said glycosidic derivative is 2-acetanido-N-(ε-aminocaproyl)-2 deoxy-β-D-glucosamine.

8. The method of claim 1, wherein said glycosidic derivative is para-aminophenyl-α-D-mannopyranoside.

9. The method of claim 1, wherein said mammalian sperm cell sample is obtained from a human.

10. The method of claim 1, wherein said incubating is conducted for at least about one hour.

11. A kit for conducting a method for evaluating the fertilization capability of mammalian sperm cells, wherein the method comprises the steps of:

capacitating a mammalian sperm cell sample;

incubating the thus-capacitated sperm cells with a conjugate of a dendrimer and a glycosidic derivative of a sugar under conditions suitable to induce an acrosome reaction in the capacitated sperm cells; and calculating the extent of the acrosome reaction in the thus-incubated sperm cells relative to a positive and a negative control, and evaluating the fertilization capability of the sperm cells as a function of the calculation, said kit comprising:

a first solution of said conjugate;

a second solution to assay for said positive control;

and a third solution to assay for said negative control, wherein each of said solutions in said kit is separately contained.

12. The kit of claim 11, further comprising a fourth solution comprising a detectable label.

13. The kit of claim 11, further comprising at least mounting device.

14. The kit of claim 11, wherein said sugar is N-acetyl-β-D-galactosamine.

15. The kit of claim 11, wherein said sugar is mannose.

16. The kit of claim 11, wherein said sugar is N-acetyl-β-D-glucosamine.

17. The kit of claim 11, wherein said glycosidic derivative is 2-acetamido-N-(ε-aminocaproyl)-2-deoxy-β-D-glucosamine.

18. The kit of claim 11, wherein said glycosidic derivative is para-aminophenyl-α-D-mannopyranoside.

19. The kit of claim 11, wherein said glycosidic derivative is p-aminophenyl-N-acetyl-β-D-glycosamide.

* * * * *

UNITED STATES PATENT AND TRADEMARK OFFICE
CERTIFICATE OF CORRECTION

PATENT NO.    : 5,736,346
DATED         : April 7, 1998
INVENTOR(S) : Tezón et al.

It is certified that error appears in the above-identified patent and that said Letters Patent is hereby corrected as shown below:

Column 2, line 18, insert --to-- immediately after "failed"
Column 2, line 24, insert --to-- immediately after "tests"
Column 3, line 51, delete the first appearing "in"
Column 5, line 59, change "see" to --See--
Column 7, line 5, insert --20-- immediately after "about"
Column 9, line 49, change "Control" to --control--
Column 10, line 4, insert --)-- immediately after "Pa. "
Column 10, line 7, change "pisum" to --Pisum--
Column 11, line 17, change "Oocytes fertilized" to --Oocytes fertilized--
Column 13, line 6, change "s" to --a--
Column 13, line 26, change "acetanido" to --acetamido--
Column 13, line 26, change "-2 deoxy-β-D-" to -- -2-deoxy-β-D- --
Column 14, line 18, change "at least" to --a--

Signed and Sealed this

First Day of September, 1998

Attest:

BRUCE LEHMAN

Attesting Officer

Commissioner of Patents and Trademarks